United States Patent [19]

Reddy et al.

[11] Patent Number: 4,596,975

[45] Date of Patent: Jun. 24, 1986

[54] THERMALLY INSULATIVE MOUNTING WITH SOLID STATE DEVICE

[75] Inventors: Padala K. Reddy, Milpitas; Hiam A. Khoury, Martinez, both of Calif.

[73] Assignee: Sierra Monitor Corporation, Sunnyvale, Calif.

[21] Appl. No.: 615,999

[22] Filed: May 31, 1984

[51] Int. Cl.$^4$ ............................................. H01L 7/00
[52] U.S. Cl. ...................................... 338/34; 73/23; 73/27 R; 361/317
[58] Field of Search .................. 338/34; 73/23, 27 R; 422/94, 95, 98, 90; 174/50.54, 52 H; 361/317, 318; 357/80; 219/209, 210

[56] References Cited

U.S. PATENT DOCUMENTS

| | | | |
|---|---|---|---|
| 3,654,579 | 4/1972 | Kurtz et al. | 338/2 |
| 3,732,519 | 5/1973 | Taguchi | 338/34 |
| 3,873,956 | 3/1975 | Kurtz et al. | 338/4 X |
| 4,030,340 | 6/1977 | Chang | 73/23 |
| 4,197,089 | 4/1980 | Willis et al. | 23/232 |
| 4,216,404 | 8/1980 | Kurtz et al. | 338/42 X |
| 4,412,203 | 10/1983 | Kurtz et al. | 338/42 X |

FOREIGN PATENT DOCUMENTS

| | | | |
|---|---|---|---|
| 52-74392 | 6/1977 | Japan | 422/98 |
| 57-23849 | 2/1982 | Japan | 73/23 |
| 57-189050 | 11/1982 | Japan | 73/23 |
| 56-86448 | 5/1983 | Japan | 73/23 |

Primary Examiner—Clarence L. Albritton
Assistant Examiner—M. M. Lateef

[57] ABSTRACT

A mounting for integrated circuit chips or solid state gas sensors, with superior thermal and electrical insulative properties. The mounting incorporates a tiny thin-wall glass capillary tube as the pedestal on which the chip or sensor is mounted. The glass tube holding the chip or sensor is then mounted on any base. A high temperature ceramic adhesive is used to hold the structure together. This method gives good mechanical support to the chip or sensor while reducing the amount of heat lost to the support structure. By using this technique, the amount of power required to heat the device to elevated temperature is vastly reduced.

11 Claims, 4 Drawing Figures

THERMALLY INSULATIVE MOUNTING WITH SOLID STATE DEVICE

DESCRIPTION

1. Technical Field

The invention relates to a technique for mounting gas sensors or integrated circuit chips with enhanced thermal insulative properties so that low power input is required.

2. Background Art

Toxic and combustible gases can be detected using semiconductor, catalytic or electrochemical sensors. Among the known systems, thin film semiconductor metal oxide sensors, which operate on the principle of adsorption and desorption of gases at the film surface, are well known. Oxidizing and reducing gases react at the film surface to produce a change in electrical conductivity which is proportional to the concentration of the gas. Thin metal oxide films such as the doped or undoped oxides of tin, tungsten, zinc and titanium must be heated to elevated temperatures, typically 150° to 500° C., to react fast enough to have practical applications. The methods used to heat such devices vary but generally include an electrically heated resistor in contact with a substrate, on which the sensing film is placed. Such a structure is shown in U.S. Pat. No. 4,030,340 to Chang. This patent shows that the chip is mounted on an inorganic foam, e.g. talc, insulative base. Other devices, such as the one shown in U.S. Pat. No. 4,197,089, apparently use heavy metal pins of high thermal conductivity to support the chip on which the heater and sensor films are placed. Such a structure places a heavy thermal drain on the heated chip and requires that high power be supplied to maintain a high operating temperature. Another device uses a resistive heater coil embedded within the center of an insulative tube with the film on the exterior of the tube. Such a device is shown in U.S. Pat. No. 3,732,519 to Taguchi. In all of these cases, the heater is generally made in different designs and the sensor film is assembled into its housing in different configurations that vary widely with the manufacturer.

The procedure used for assembling the heater and the sensor film into a package is of considerable importance in view of the high temperature operation of the device. Heating the sensor film by a resistive heating coil inside of an insulative tube is least preferred in view of the large thermal losses due to radiation from a large surface area. Also, such devices are supported by additional wires which function as the sensor film electrical connectors. Wire heavy enough to support such a device also functions as an efficient heat sink and transfers heat to the support structure. On the other hand, direct heating which uses a heater integrated within the sensing device is preferred only when the sensing device is assembled by using proper thermal insulating materials to support the device. Poor thermal insulation results in loss of heat from the device to the package that will in turn increase the device operating power requirements to unacceptable levels. Sensing devices with large power requirements are less preferred as they do not lend themselves to field monitors. In addition, a high amount of electrical power is likely to damage the tiny resistive heater element integrated within the device due to thermal and electrical stress.

The present invention involved a search for a more suitable mounting material. While inorganic foams serve the desired purpose, there is a need for a material and a method for mounting gas sensors and integrated circuit chips that gives acceptable mechanical support and which also provides insulative properties necessary to operate the devices at elevated temperatures without excessive power drain.

SUMMARY OF THE INVENTION

The above object has been achieved with a new mounting technique featuring a rigid tube of thermally insulating material supporting a heated chip or gas sensor above a standard base. Preferably the tube is a thin wall glass capillary which is cemented in place. The glass tube provides the needed structural support while conducting little heat away, much less than materials of prior art. The choice of materials of low thermal conductivity to support the device allows the device to operate at a lower power input.

The apparatus is composed of a base, such as a transistor only header, a glass support tube, and the sensor element or semiconductor chip. It operates on direct heat from a resistance heater integrated onto the sensor element or chip. Electrical connections are made by thin wires from the surface of the sensor element or chip to pins comprising a part of the base. These connections are made to both the active device and the heater with thin gold wires using techniques known to those skilled in the art. By using this assembly method the heat loss is nearly limited to thermal conduction along the thin wires used for the electrical connections.

BEST MODE FOR CARRYING OUT THE INVENTION

Figure 1:
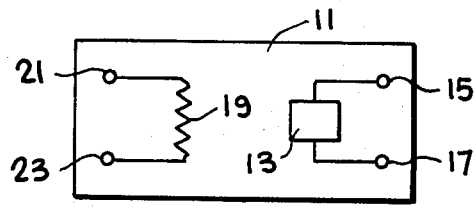
FIG. 1 is the top view of a simplified sensor die showing a resistive heater element and a sensing element.

With reference to FIG. 1, the sensing device, hereafter referred to as the die 11 on which the gas sensor and heater are integrated, is shown in simplified form. This die could also be an integrated circuit chip of a type requiring heating or thermal stabilization. The die has at least one functional circuit represented by block 13, with terminals 15 and 17. The die also carries a resistive heater element 19 having terminals 21 and 23. For purposes of discussion in this application, the functional circuit represents a semiconducting gas sensor. Such a sensor typically comprises a thin film of metal oxide spanning a pair of spaced apart electrodes. The metal oxide has the effect of exhibiting a change in electrical conductivity in the presence of oxidizing or reducing gases. By measuring the change in conductivity between electrodes, a direct measure of gas concentration may be obtained. Typically, a die of the type shown in FIG. 1 has an edge dimension of 75 mils on a side and may be square or rectangular.

Figure 2:
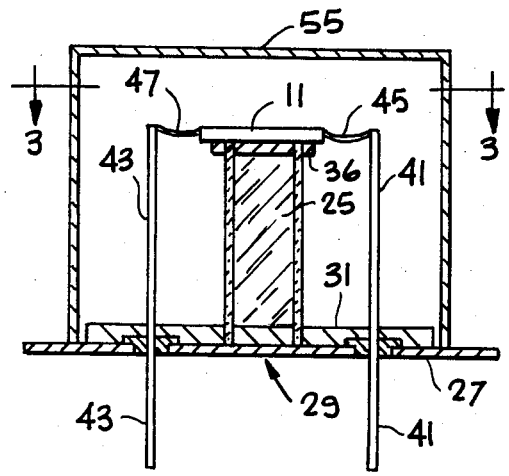
FIG. 2 is a side sectional view of the device assembly of the present invention.

In FIG. 2, the die 11 is shown to be mounted on a glass tube 25 which is supported on a base 27, hereafter referred to as a header. For this application a standard TO-5 header was used. The tube 25 is preferably a hollow glass capillary, although tubes or rods of materials such as ceramics could be used. The important consideration is that the tube have good mechanical strength to the extent that it is self-supporting and that it have good thermal insulation properties. Glass and some ceramics meet both of these qualifications. The material used for the tube is preferably a tiny thin-wall Pyrex capillary with an outside diameter of 1.5 to 1.8 mm and a thin wall thickness of approximately 0.25 mm. Pyrex is a registered trademark for heat treated glass. Other refractive materials of the same kind will work. Tubes were cut into small pieces of length 80 mils. Although it is helpful to use longer tube, the length is restricted by the height of the pins 41 and 43 of the header. The lower end 29 of tube 25 is fixed in place by means of a thin layer of an adhesive 31, serving to cement tube 25 in place. A thin layer of adhesive is typically applied to header 27 and the glass tube 25 is placed into position. The zirconia based adhesive used in this process is allowed to dry and then baked at 150° C. for 30 minutes. The adhesive is then applied to the back side of the die 11 and the die is placed atop the tube 25. Using a special tool, the die is gently positioned to the center of the tube, allowed to dry, and the bake cycle is repeated.

Header 27 contains four pins 41 and 43, only two of which can be seen in this view, which extend upward above the base and down through the base. These pins are the electrical leads which carry current to and from the sensor die 11, including power for the resistive heating element. The wire pins 41 and 43 are generally parallel and spaced a slight distance from the edges of the die 11. The portions 41 and 43 have an upward height approximately coextensive with the height of tube 25. The die 11 has peripheral bonding pads to which 1.0 to 1.2 mil gold wires 45 and 47 are connected for making contact with the pins 41 and 43. These connecting wires 45 and 47 have no mechanical strain thereon, but should be kept short. Over the outer periphery of the base, an enclosure cap 55 is situated which may be a porous sintered metal flame arrestor. Cap 55 provides some thermal insulation of die, as well as protecting the mechanical assembly, yet is permeable to gas being detected. The cap is slightly spaced away from the electrodes, the die and the tube.

Figure 3:
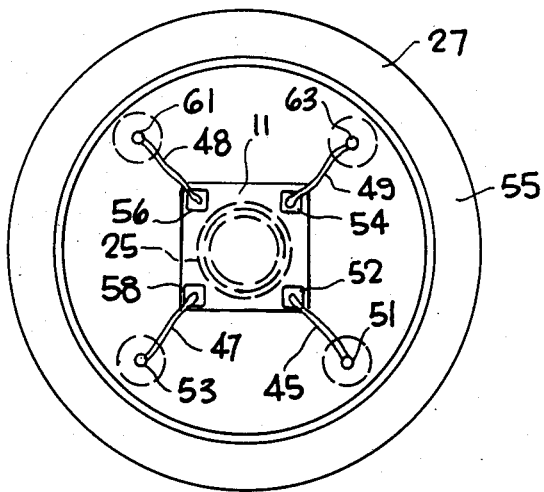
FIG. 3 is a top view taken along lines 3—3 in FIG. 2.

In FIG. 3, header 27 is seen to have upwardly extending wire pins 51, 53, 61 and 63. These are connected to die 11 by means of bonding pads 52, 54, 56 and 58. Very fine gold wires 45, 47, 48 and 49 connect the pins to the bonding pads on the die, supported by tube 25, indicated by dashed lines.

Figure 4:
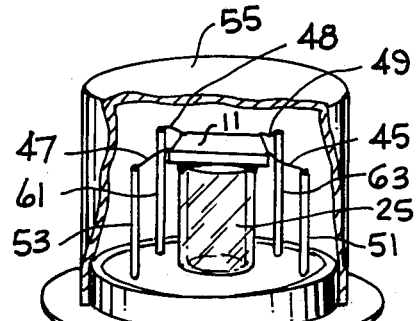
FIG. 4 is a perspective view of the device assembly shown in FIG. 2.

In FIG. 4 is shown a die 11 having an underside which is supported by a hollow tube 25. A hollow tube provides excellent mechanical support for the device. The bonding pads near the edges of the die are seen connected to the base pins 51, 53, 61 and 63 by means of fine wires 45, 47, 48 and 49. The base pins extend through the base and may serve as electrical leads for insertion into a receptable or connection to other circuit components by any joining techniques such as soldering or wire wrapping.

We claim:

1. A thermally insulated solid state gas sensor and mounting comprising,
    a base having a plurality of electrode wires extending therethrough in insulated relationship to each other and to the base, said electrode wires having a portion extending outwardly from the base and a portion extending upwardly above the base,
    a hollow, self-supporting tube of thermally insulative material having a first end connected to the base and a second end extending upwardly from the base, and
    a solid state gas sensor having a heating element forming a portion of the sensor, the sensor mounted atop said tube of thermally insulative material, said sensor having bonding regions electrically connected to said electrode wires.

2. The apparatus of claim 1 wherein said tube of thermally insulative material is glass.

3. The apparatus of claim 1 wherein said tube of thermally insulative material is ceramic.

4. The apparatus of claim 1 wherein said electrical heating means comprises a heating element forming a portion of the device.

5. The apparatus of claim 1 wherein said tube of thermally insulative material has approximately the same height above the base as the portion of said electrode wires above the base.

6. The apparatus of claim 1 wherein the wall thickness of said tube is less than 0.35 mm.

7. A thermally insulated solid state device and mounting comprising,
    a solid state device having peripheral bonding pads, and an underside,
    heater means on said device for heating the device in the range of 150° C. to 500° C.,
    a hollow, self-supporting tube of thermally insulative material attached to the underside of the device at a first end of the tube,
    a base associated with a plurality of electrode wires extending away from the base, said device having electrical wires connecting said bonding pads, said electrodes, and said heater means, said tube being connected to said base at a second end of said tube and extending upwardly from said base toward said first end, and
    a protective cap slightly spaced from said device and covering the base to form a protective enclosure about said device, said tube and said electrical wires connecting said bonding pads and said electrodes.

8. The apparatus of claim 7 wherein said solid state device is a gas sensor.

9. In a heat insulative mounting having a solid state device therein having a self-contained heating element and mounted in a container having a base, electrodes and a protective gas permeable cap, the improvement in the insulative mounting comprising,
    a thin-wall self-supporting hollow capillary tube of thermally insulative material having a first end connected to a base of a container and a second end supporting said solid state device having a heating element associated therewith, said heating element capable of heating the device in the range of 150° C. to 500° C. and
    thin electrical wires connecting the solid state device to said electrodes of said container.

10. A thermally insulated solid state device and mounting comprising,
    a base having a plurality of electrode wires extending therethrough in insulated relationship to each other and to the base, said electrode wires having a portion extending outwardly from the base and a portion extending upwardly above the base,
    a cap covering the base,
    a hollow, self-supporting tube of thermally insulative material having a first end connected to the base and a second end extending upwardly from the base toward said cap, a solid state device having an underside mounted atop said tube of thermally insulative material, spaced apart from the cap, said device having a side opposite said underside facing the cap, away from said tube, with bonding regions electrically connected to said electrode wires and to electrical means on said device for heating said device.

11. The apparatus of claim 10 wherein said tube of thermally insulative material has approximately the same height above the base as the portion of said electrode wires above the base.

* * * * *